United States Patent
Yeh

(10) Patent No.: US 7,125,974 B2
(45) Date of Patent: Oct. 24, 2006

(54) VIRAL SEQUENCES

(76) Inventor: Chau-Ting Yeh, Liver Research Unit, Chang Gung Memorial Hospital, 199 Tung Hwa North Road, Taipei 105 (TW)

( * ) Notice: Subject to any disclaimer, the term of this patent is extended or adjusted under 35 U.S.C. 154(b) by 123 days.

(21) Appl. No.: 10/730,632

(22) Filed: Dec. 8, 2003

(65) Prior Publication Data

US 2004/0219518 A1 Nov. 4, 2004

Related U.S. Application Data

(60) Provisional application No. 60/440,948, filed on Jan. 17, 2003.

(51) Int. Cl.
*C07H 21/04* (2006.01)
*C12N 5/02* (2006.01)

(52) U.S. Cl. ...................... 536/23.1; 435/325

(58) Field of Classification Search ............ None
See application file for complete search history.

(56) References Cited

OTHER PUBLICATIONS

Hausen H, Oncogenic DNA viruses, 2001, Oncogene, vol. 20, pp. 7820-7823.*

Scaglioni PP, Posttranscriptional regulation of hepatitis B virus replication by the precore protein, 1997, J. of Virology, vol. 71, pp. 345-353.*

Elizabetta Bugianiesi et al. "Expanding the Natural History of Nonalcoholic Steatohepatitis: From Cryptogenic Cirrhosis to Hepatocellular Carcinoma". Gastroenterology 123:134-140, 2002.

Jia-Horng Kao et al. "GB Virus-C/Hepatitis G Virus Infection in an Area Endemic for Viral Hepatitis, Chronic Liver Disease, and Liver Cancer". Gastroenterology 112:1265-1270, 1997.

Akihiro Matsumoto et al. "Transfusion-Associated TT Virus Infection and Its Relationship to Liver Disease". Heptology 30:283-288, 1999.

Fedja A. Rochling et al. "Acute Sporadic Non-A, Non-B, Non-C, Non-D, Non-E Hepatitis". Hepatology 25:478-483, 1997.

Takeji Umemura et al. "SEN Virus: Response to Interferon Alfa and Influence on the Severity and Treatment Response of Coexistent Hepatitis C". Hepatology 35:953-959, 2002.

* cited by examiner

*Primary Examiner*—Dave Trong Nguyen
*Assistant Examiner*—David A. Montanari
(74) *Attorney, Agent, or Firm*—Fish & Richardson P.C.

(57) ABSTRACT

An isolated nucleic acid comprising a nucleotide sequence at least 70% identical to SEQ ID NO:1, or a complementary sequence thereof. Presence of the nucleic acid in a subject predisposes the subject to an abnormal liver condition, an adenocarcinoma, or a combination thereof. Also disclosed are a method of diagnosing such diseases, a method of identifying a compound for treating such diseases, and a method of treating such diseases.

4 Claims, No Drawings

VIRAL SEQUENCES

RELATED APPLICATION

This application claims priority to U.S. application Ser. No. 60/440,948 filed on Jan. 17, 2003, the contents of which are incorporated herein by reference.

BACKGROUND

Hepatitis is caused by viruses. Several types of hepatitis viruses have been identified. Among them, hepatitis A and B viruses are the most common. Four other known hepatitis viruses are designated as hepatitis C, D, E, and G. Hepatitis A and E viruses only cause acute infection, while hepatitis B and C are chronic illness. Hepatitis D virus is only present in patients co-infected with hepatitis B. However, the etiology of a substantial number of patients with acute and chronic hepatitis remains unknown. Thus, identification of additional causative agents is needed.

SUMMARY

This invention relates to a novel nucleotide sequence found to be present in a subject with an abnormal liver condition, an adenocarcinoma, or a combination thereof at a frequency higher than that for a normal subject. This nucleotide sequence (designated as "NV-F;" SEQ ID NO:1) is shown below:

```
  1 gac tgt tgg tgg cac aaa gcc ccg agc aaa gtt ggc aac ccc cgc cgt cac tca gcc ctg
    D   C   W   W   H   K   A   P   S   K   V   G   N   P   R   R   H   S   A   L    20

61 caa gaa gcc act tgc gtc ctc cac aac tcc cca aag ttg tta ctg gtg tac caa tcg gag
    Q   E   A   T   C   V   L   H   N   S   P   K   L   L   L   V   Y   Q   S   E    40

121 gca gcc gag ggg atg tat aaa gaa ata gca aag gaa ttc gcg aaa ggg aaa gga aag aag
    A   A   E   G   M   Y   K   E   I   A   K   E   F   A   K   G   K   G   K   K    60

181 gag agg aaa cta aag aag aaa aaa atg ctt tcg ggt att acg gaa gaa ggt tct cca cag
    E   R   K   L   K   K   K   K   M   L   S   G   I   T   E   E   G   S   P   Q    80

241 cag tcc tct tct gct ccg ggc ctg gag gga gag agc gag acc aca aag atg atg agc aaa
    Q   S   S   S   A   P   G   L   E   G   E   S   E   T   T   K   M   M   S   K   100

301 aaa ttc caa gac atg acg aat ccg caa aag aag aaa aag aaa cgg acc agt ctg ctc ctt
    K   F   Q   D   M   T   N   P   Q   K   K   K   K   R   T   S   L   L   L       120

361 aac t   (SEQ ID NO:1)
    N       (SEQ ID NO:2)
```

The nucleic acid of SEQ ID NO:1 contains an incomplete open reading frame that has 121 amino acids. The amino acid sequence encoded by SEQ ID NO:1 is designated as SEQ ID NO:2.

Accordingly, the invention features an isolated nucleic acid containing a nucleotide sequence at least 70% identical to SEQ ID NO:1, or a complementary sequence thereof. The percent identity can be anywhere between and including 70% and 100%, e.g., 75%, 80%, 85%, 90%, and 95%. Presence of the nucleic acid in a subject predisposes the subject to an abnormal liver condition (e.g., hepatitis A–E, non-A–E hepatitis, or a combination thereof), an adenocarcinoma (e.g., colon cancer or lung cancer), or a combination thereof. A nucleic acid of the invention can be used as a DNA vaccine for treating such diseases.

An "isolated nucleic acid" is a nucleic acid the structure of which is not identical to that of any naturally occurring nucleic acid or to that of any fragment of a naturally occurring genomic nucleic acid. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein.

The "percent identity" of two sequences is determined using the algorithm of Karlin and Altschul ((1990) Proc. Natl. Acad. Sci. USA 87, 2264–2268), modified as in Karlin and Altschul ((1993) Proc. Natl. Acad. Sci. USA 90, 5873–5877). Such an algorithm is incorporated into the XBLAST programs of Altschul et al. ((1990) J. Mol. Biol. 215, 403–410). BLAST searches are performed with the XBLAST program, score=50, wordlength=3. Where gaps exist between two sequences, Gapped BLAST is utilized as described in Altschul et al. ((1997) Nucleic Acids Res. 25, 3389–3402). When utilizing BLAST and Gapped BLAST programs, the default parameters of the respective programs (e.g., XBLAST) are used. See the World Wide Web at ncbi.nlm.nih.gov.

The invention also features a pure polypeptide containing an amino acid sequence encoded by a nucleic acid of the invention. A polypeptide of the invention can be used as a protein vaccine for treating an abnormal liver condition, an adenocarcinoma, or a combination thereof. It can also be used for producing antibodies (either monoclonal or polyclonal) against a polypeptide of the invention. These antibodies in turn are useful for detecting the presence and distribution of the polypeptide in tissues and in cellular compartments. For example, such antibodies can be used to verify the expression of the polypeptide in a transgenic animal.

A "pure polypeptide" refers to a polypeptide substantially free from naturally associated molecules, i.e., it is at least 75% (e.g., at least 80, 85, 90, or 95; or 100%) pure by dry weight. Purity can be measured by any appropriate standard method, for example, by column chromatography, polyacrylamide gel electrophoresis, or HPLC analysis.

The invention further features an isolated nucleic acid characterized in that it hybridizes under stringent conditions to SEQ ID NO:1, or a complementary sequence thereof, as well as a cell (in a culture or in a transgenic animal) containing a nucleic acid of the invention. Such a nucleic acid can be at least 15 (e.g., at least 30, 50, 100, 200, 500, or 1000) nucleotides in length. An example of a nucleic acid within the invention is an isolated nucleic acid (e.g., a vector) encoding a polypeptide of the invention. These nucleic acids and cells can be used for producing the polypeptides of the invention or generating a transgenic animal. The nucleic acids can also be used as primers in detection methods based on PCR or primer extension, or as labeled probes in nucleic acid blots (e.g., Northern blots).

By hybridization under "stringent conditions" is meant hybridization at 65° C., 0.5×SSC, followed by washing at 45° C., 0.1×SSC.

In addition, the invention features a method of (1) expressing in a cell a transcript, i.e., transcript I, that hybridizes under above-described stringent conditions to SEQ ID NO:1, or (2) expressing in a cell a transcript, i.e., transcript II, that is complementary to transcript I. Transcript I, when expressed in a cell, can serve as an anti-sense RNA that binds to endogenous NV-F mRNA to prevent it from being translated into a functional protein. Therefore, this method can be used in gene therapy for treating an abnormal liver condition, an adenocarcinoma, or a combination thereof. Transcript II can encode an NV-F protein, and when expressed in a cell, is translated into an NV-F protein. Thus, this method can be used for producing a polypeptide of the invention.

NV-F has been found to be present at a higher than normal frequency in subjects with non-A–E hepatitis, hepatitis B, hepatitis C, or colon cancer. It is thus useful for diagnosing and treating such diseases.

In one aspect, this invention features a method of determining whether a subject is suffering from or at risk for developing an abnormal liver condition, an adenocarcinoma, or a combination thereof. The method involves providing a sample from a subject and detecting in the sample a nucleic acid containing SEQ ID NO:1, a transcript thereof, or a polypeptide containing SEQ ID NO:2. Presence of the nucleic acid, the transcript, or the polypeptide in the sample indicates that the subject is suffering from or at risk for developing an abnormal liver condition, an adenocarcinoma, or a combination thereof. The nucleic acid, the transcript, and the polypeptide can be detected, e.g., by PCR, Northern blot, and Western blot, respectively, or by any other methods known in the art.

In another aspect, this invention features a method of identifying a compound for preventing and treating an abnormal liver condition, an adenocarcinoma, or a combination thereof. The method involves contacting a compound with a cell having a nucleic acid that contains SEQ ID NO:1, a transcript thereof, of a polypeptide that contains SEQ ID NO:2, and determining a level of the nucleic acid, the transcript, or the polypeptide in the cell. If the level of the nucleic acid, the transcript, or the polypeptide in the presence of the compound is lower than that in the absence of the compound, it indicates the compound is a candidate for preventing and treating an abnormal liver condition, an adenocarcinoma, or a combination thereof. Production of a compound thus identified is also within the scope of the invention.

In still another aspect, this invention features a method of preventing and treating an abnormal liver condition, an adenocarcinoma, or a combination thereof. The method involves identifying a subject suffering from or being at risk for developing an abnormal liver condition, an adenocarcinoma, or a combination thereof and having a nucleic acid that contains SEQ ID NO:1, a transcript thereof, or a polypeptide that contains SEQ ID NO:2, and administering to the subject an effective amount of a composition to decrease a level of the nucleic acid, the transcript, or the polypeptide in the subject. "Treatment of an abnormal liver condition, an adenocarcinoma, or a combination thereof" herein refers to administering a composition to a subject, who has an abnormal liver condition, an adenocarcinoma, or a combination thereof, a symptom of such diseases or a predisposition towards such diseases, with the purpose to cure, relieve, alter, affect, or prevent the abnormal liver condition, an adenocarcinoma, or a combination thereof, the symptom of them, or the predisposition towards them.

Also within the scope of this invention is a pharmaceutical composition for preventing and treating an abnormal liver condition, an adenocarcinoma, or a combination thereof. The composition can contain a pharmaceutically acceptable carrier and a nucleic acid encoding a transcript (i.e., an anti-sense RNA) characterized in that it hybridizes under stringent conditions to SEQ ID NO:1 or an antibody against the polypeptide of SEQ ID NO:2.

The details of one or more embodiments of the invention are set forth in the accompanying description below. Other features, objects, and advantages of the invention will be apparent from the detailed description, and from the claims.

DETAILED DESCRIPTION

This invention is based on the discovery of a novel nucleotide sequence (NV-F) in a patient with non-A–E hepatitis and colon cancer. Unexpectedly, NF-V was later detected in 6.7% of healthy individuals and in 23.5%, 54%, 44%, and 23.3% of patients with chronic non-A–E hepatitis, chronic hepatitis B, chronic hepatitis C, and colon cancer, respectively. NV-F was resistant to RNase A digestion but was sensitive to DNase I digestion. CsCl gradient analysis showed that NV-F was present in particles with buoyant densities of about 1.33–1.39 and 1.21–1.25 g/ml. These results indicate that NV-F is a DNA virus associated with an abnormal liver condition, an adenocarcinoma, or a combination thereof.

In one aspect, the present invention features NV-F nucleic acids (i.e., DNA, cDNA, and RNA) characterized in that they hybridize under stringent conditions to SEQ ID NO:1, or a complementary sequence thereof. Examples of NV-F nucleic acids include those containing a nucleotide sequence at least 70% identical to SEQ ID NO:1, or a complementary sequence thereof. Presence of these nucleic acids in a subject predisposes the subject to an abnormal liver condition, an adenocarcinoma, or a combination thereof.

In another aspect, the invention features pure NV-F polypeptides (e.g., SEQ ID NO:2) encoded by the above-described NV-F nucleic acids, including functional NV-F polypeptides. A "functional polypeptide" refers to a polypeptide which possesses biological activity equivalent to that of a wild-type NV-F protein, e.g., a fragment of a wild-type NV-F protein.

A nucleic acid of the invention can be expressed in vitro by DNA transfer into a suitable host cell by methods known in the art. For example, the nucleic acid can be inserted into a recombinant expression vector. A variety of host-expression vector systems can be utilized to express a nucleic acid of the invention. These include, but are not limited to, microorganisms such as bacteria transformed with recombinant bacteriophage DNA, plasmid DNA, or cosmid DNA expression vectors; yeast transformed with recombinant yeast expression vectors; and human cell lines infected with recombinant virus or plasmid expression vectors. Isolation and purification of recombinant polypeptides, or fragments thereof, provided by the invention, can be carried out by conventional means including preparative chromatography and immunological separations involving monoclonal or polyclonal antibodies.

The invention also features antibodies against NV-F polypeptide, including monoclonal antibodies and polyclonal antibodies. The term "antibody" includes intact molecules as well as fragments thereof, such as Fab, F(ab')$_2$, and Fv which are capable of binding to an epitopic determinant present in the NV-F polypeptide. Methods of making monoclonal and polyclonal antibodies and fragments thereof are known in the art. See, for example, Harlow and Lane (1988) Antibodies: A Laboratory Manual, Cold Spring Harbor Laboratory, New York.

In addition, the invention provides methods for diagnosing and treating an abnormal liver condition, an adenocarcinoma, or a combination thereof, and identifying therapeutic compounds for treating such diseases using NV-F nucleic acids and polypeptides.

A diagnostic method of this invention involves detecting NV-F DNA, mRNA, or protein in a sample prepared from a subject. Presence of the NV-F DNA, mRNA, or protein indicates that the subject is suffering from or at risk for developing an abnormal liver condition, an adenocarcinoma, or a combination thereof. The methods of this invention can be used on their own or in conjunction with other procedures to diagnose an abnormal liver condition, an adenocarcinoma, or a combination thereof, in appropriate subjects.

The NV-F DNA sequence can be detected by a variety of methods known in the art. For example, it can be identified by PCR amplification or Southern blot analysis of genomic DNA prepared from a test sample.

Methods of detecting an mRNA molecule in a sample are known in the art. In order to measure mRNA levels, cells can be lysed and the levels of NV-F mRNA in the lysates or in RNA purified or semi-purified from the lysates can be determined by any of a variety of methods including, without limitation, hybridization assays using detectably labeled NV-F-specific DNA or RNA probes and quantitative or semi-quantitative RT-PCR methodologies using appropriate NV-F-specific oligonucleotide primers. Alternatively, quantitative or semi-quantitative in situ hybridization assays can be carried out using, for example, tissue sections or unlysed cell suspensions, and detectably (e.g., fluorescently or enzyme) labeled DNA or RNA probes. Additional methods for quantifying mRNA include RNA protection assay (RPA) and SAGE.

Methods of detecting a protein in as ample are also known in the art. Many such methods employ antibodies (e.g., monoclonal or polyclonal antibodies) that bind specifically to the NV-F protein. In such assays, the antibody itself or a secondary antibody that binds to it can be detectably labeled. Alternatively, the antibody can be conjugated with biotin, and detectably labeled avidin (a polypeptide that binds to biotin) can be used to detect the presence of the biotinylated antibody. Combinations of these approaches (including "multi-layer sandwich" assays) familiar to those in the art can be used to enhance the sensitivity of the methodologies. Some of these protein-measuring assays (e.g., ELISA or Western blot) can be applied to lysates of cells, and others (e.g., immunohistological methods or fluorescence flow cytometry) applied to histological sections or unlysed cell suspensions. Methods of measuring the amount of label depend on the nature of the label and are well known in the art. Appropriate labels include, without limitation, radionuclides (e.g., $^{125}$I, $^{131}$I, $^{35}$S, $^{3}$H, or $^{32}$P), enzymes (e.g., alkaline phosphatase, horseradish peroxidase, luciferase, or β-glactosidase), fluorescent moieties or proteins (e.g., fluorescein, rhodamine, phycoerythrin, GFP, or BFP), or luminescent moieties (e.g., Qdot™ nanoparticles supplied by the Quantum Dot Corporation, Palo Alto, Calif.). Other applicable assays include quantitative immunoprecipitation or complement fixation assays.

The invention also provides a method for identifying and manufacturing compounds (e.g., proteins, peptides, peptidomimetics, peptoids, antibodies, or small molecules) that reduce the level of NV-F DNA, mRNA, or protein in a cell. Compounds thus identified can be used, e.g., for preventing and treating an abnormal liver condition, an adenocarcinoma, or a combination thereof.

The candidate compounds of the present invention can be obtained using any of the numerous approaches in combinatorial library methods known in the art. Such libraries include: peptide libraries, peptoid libraries (libraries of molecules having the functionalities of peptides, but with a novel, non-peptide backbone that is resistant to enzymatic degradation); spatially addressable parallel solid phase or solution phase libraries; synthetic libraries obtained by deconvolution or affinity chromatography selection; and the "one-bead one-compound" libraries. See, e.g., Zuckermann et al. (1994) J. Med. Chem. 37, 2678–85; and Lam (1997) Anticancer Drug Des. 12, 145.

Examples of methods for the synthesis of molecular libraries can be found in the art, for example, in: DeWitt et al. (1993) PNAS USA 90, 6909; Erb et al. (1994) PNAS USA 91, 11422; Zuckermann et al. (1994) J. Med. Chem. 37, 2678; Cho et al. (1993) Science 261, 1303; Carrell et al. (1994) Angew. Chem. Int. Ed. Engl. 33, 2059; Carell et al. (1994) Angew. Chem. Int. Ed. Engl. 33, 2061; and Gallop et al. (1994) J. Med. Chem. 37, 1233.

Libraries of compounds may be presented in solution (e.g., Houghten (1992) Biotechniques 13, 412–421), or on beads (Lam (1991) Nature 354, 82–84), chips (Fodor (1993) Nature 364, 555–556), bacteria (Ladner, U.S. Pat. No. 5,223,409), spores (Ladner, U.S. Pat. No. 5,223,409), plasmids (Cull et al. (1992) PNAS USA 89, 1865–1869), or phages (Scott and Smith (1990) Science 249, 386–390; Devlin (1990) Science 249, 404–406; Cwirla et al. (1990) PNAS USA 87, 6378–6382; Felici (1991) J. Mil. Biol. 222, 301–310; and Ladner supra).

To identify compounds that reduce the level of NV-F DNA, mRNA, or protein in a cell, a cell is contacted with a candidate compound and the level of the NV-F DNA, mRNA, or protein is evaluated relative to that in the absence of the candidate compound. The cell can be a cell that contains the NV-F sequence yet does not naturally expresses it, a cell that naturally expresses NV-F, or a cell that is modified to express a recombinant nucleic acid, for example, having the NV-F sequence fused to a marker gene. The level of the NV-F or the marker DNA, mRNA, or protein can be determined by methods described above and any other methods well known in the art. If the level of the NV-F or the marker DNA, mRNA, or protein is lower in the presence of the candidate compound than that in the absence of the candidate compound, the candidate compound is identified as a potential drug for preventing and treating an abnormal liver condition, an adenocarcinoma, or a combination thereof.

This invention also provides a method for preventing and treating an abnormal liver condition, an adenocarcinoma, or a combination thereof. Subjects to be treated can be identified, for example, by detecting NV-F DNA, mRNA, or protein in a sample prepared from a subject by methods described above. If the NV-F DNA, mRNA, or protein is present in the sample, the subject is a candidate for treatment with an effective amount of a compound that reduces the level of NV-F DNA, mRNA, or protein in the subject. This method can be performed alone or in conjunction with other drugs or therapy.

In one in vivo approach, a therapeutic composition (e.g., a composition containing a compound that reduces the level of NV-F DNA, mRNA, or protein in a cell) is administered to the subject. Generally, the compound will be suspended in a pharmaceutically acceptable carrier (e.g., physiological saline) and administered orally or by intravenous infusion, or injected or implanted subcutaneously, intramuscularly, intrathecally, intraperitoneally, intrarectally, intravaginally, intranasally, intragastrically, intratracheally, or intrapulmonarily.

The dosage required depends on the choice of the route of administration; the nature of the formulation; the nature of the subject's illness; the subject's size, weight, surface area, age, and sex; other drugs being administered; and the judgment of the attending physician. Suitable dosages are in the range of 0.01–100.0 mg/kg. Wide variations in the needed dosage are to be expected in view of the variety of compounds available and the different efficiencies of various routes of administration. For example, oral administration would be expected to require higher dosages than administration by intravenous injection. Variations in these dosage levels can be adjusted using standard empirical routines for optimization as is well understood in the art. Encapsulation of the compound in a suitable delivery vehicle (e.g., polymeric microparticles or implantable devices) may increase the efficiency of delivery, particularly for oral delivery.

Alternatively, a polynucleotide containing a nucleic acid sequence encoding an anti-sense NV-F RNA can be delivered to the subject, for example, by the use of polymeric, biodegradable microparticle or microcapsule delivery devices known in the art.

Another way to achieve uptake of the nucleic acid is using liposomes, prepared by standard methods. The vectors can be incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells (Cristiano et al. (1995) J. Mol. Med. 73, 479). Alternatively, tissue specific targeting can be achieved by the use of tissue-specific transcriptional regulatory elements (TRE) which are known in the art. Delivery of "naked DNA" (i.e., without a delivery vehicle) to an intramuscular, intradermal, or subcutaneous site is another means to achieve in vivo expression.

In the relevant polynucleotides (e.g., expression vectors), the nucleic acid sequence encoding an anti-sense NV-F RNA is operatively linked to a promoter or enhancer-promoter combination. Enhancers provide expression specificity in terms of time, location, and level. Unlike a promoter, an enhancer can function when located at variable distances from the transcription initiation site, provided a promoter is present. An enhancer can also be located downstream of the transcription initiation site.

Suitable expression vectors include plasmids and viral vectors such as herpes viruses, retroviruses, vaccinia viruses, attenuated vaccinia viruses, canary pox viruses, adenoviruses and adeno-associated viruses, among others.

Polynucleotides can be administered in a pharmaceutically acceptable carrier. Pharmaceutically acceptable carriers are biologically compatible vehicles that are suitable for administration to a human, e.g., physiological saline or liposomes. A therapeutically effective amount is an amount of the polynucleotide that is capable of producing a medically desirable result (e.g., a reduced level of NV-F DNA, mRNA, or protein) in a treated subject. As is well known in the medical arts, the dosage for any one subject depends upon many factors, including the subject's size, body surface area, age, the particular compound to be administered, sex, time and route of administration, general health, and other drugs being administered concurrently. Dosages will vary, but a preferred dosage for administration of polynucleotide is from approximately $10^6$ to $10^{12}$ copies of the polynucleotide molecule. This dose can be repeatedly administered, as needed. Routes of administration can be any of those listed above.

The present invention further features a pharmaceutical composition that contains a pharmaceutically acceptable carrier and an effective amount of a compound that reduces the level of NV-F DNA, mRNA, or protein in the subject. For example, the compound can be a nucleic acid encoding a transcript characterized in that it hybridizes under stringent conditions to SEQ ID NO:1, or an antibody against the polypeptide of SEQ ID NO:2. The pharmaceutical composition can be used to prevent and treat an abnormal liver condition, an adenocarcinoma, or a combination thereof.

The pharmaceutically acceptable carrier includes a solvent, a dispersion medium, a coating, an antibacterial and antifungal agent, and an isotonic and absorption delaying agent. An "effective amount" is the amount required to conifer therapeutic effect. The interrelationship of dosages for animals and humans (based on milligrams per meter squared of body surface) is described by Freireich et al. (1966) Cancer Chemother. Rep. 50:219. Body surface area can be approximately determined from height and weight of the subject. See, e.g., p537, Scientific Tables, Geigy Pharmaceuticals, Ardley, N.Y., 1970. Effective doses also vary, as recognized by those skilled in the art, dependent on route of administration, excipient usage, and the like.

A pharmaceutical composition of the invention can be formulated into dosage forms for different administration routes utilizing conventional methods. For example, it can be formulated in a capsule, a gel seal, or a tablet for oral administration. Capsules can contain any standard pharmaceutically acceptable materials such as gelatin or cellulose. Tablets can be formulated in accordance with conventional procedures by compressing chitosan with a solid carrier and a lubricant. Examples of solid carriers include starch and sugar bentonite. A pharmaceutical composition of the invention can also be administered in a form of a hard shell tablet or a capsule containing a binder, e.g., lactose or mannitol, a conventional filler, and a tableting agent. The pharmaceutical composition can be administered via the parenteral route. Examples of parenteral dosage forms include aqueous solutions, isotonic saline or 5% glucose of the active agent, or other well-known pharmaceutically acceptable excipient. Cyclodextrins, or other solubilizing agents well known to those familiar with the art, can be utilized as pharmaceutical excipients for delivery of the therapeutic agent.

The efficacy of a pharmaceutical composition of the invention can be evaluated both in vitro and in vivo. Briefly, the composition can be tested in vitro for its ability to reduces the level of NV-F DNA, mRNA, or protein in a cell.

For in vivo studies, the composition can be injected into an animal and its inhibitory effects on an abnormal liver condition, an adenocarcinoma, or a combination thereof, are then accessed. Based on the results, an appropriate dosage range and administration route can be determined.

The specific example below is to be construed as merely illustrative, and not limitative of the remainder of the disclosure in any way whatsoever. Without further elaboration, it is believed that one skilled in the art can, based on the description herein, utilize the present invention to its fullest extent. All publications recited herein are hereby incorporated by reference in their entirety.

Materials and Methods

1. Patients

A 66 years old male (Patient-L) suffered from colon cancer (adenocarcinoma in transverse colon). He received colectomy which was subsequently complicated with anastomosis leakage, sepsis, and gastric ulcer bleeding. After treatment, the patient's conditions were stabilized. Unfortunately, an episode of acute hepatitis (peak GPT 284 U/L) with deep jaundice (bilirubin 19 mg/ml) occurred. However, no known viral markers were detected. A novel viral sequence (NV-F) was later identified in serum obtained from this patient.

Serum samples from 5 groups of other subjects were used for NV-F screening assay. These subjects include 150 normal people (from Health Examination Center) with normal GPT and no identifiable HBV or HCV markers, 50 patients with chronic hepatitis B, 50 patients with chronic hepatitis C, 30 patients with biopsy-proved colon cancer, and 68 patients with chronic non-A–E hepatitis.

2. Serological Study

Hepatitis B surface antigen (HBsAg), total or immunoglobulin M class serum antibody to hepatitis A virus (anti-HAV), and serum antibody to hepatitis D virus (anti-HDV) were assayed using radioimmunoassay kits (Ausria-II, HAVAB or HAVAB-M, and Anti-Delta; Abbott Laboratories, North Chicago, Ill.). Antibody to hepatitis C virus was detected using an enzyme immunoassay kit (HCV-II; Abbott Laboratories, North Chicago, Ill.). HCV-RNA was detected by an RT-PCR assay (Amplicor® HCV testl Roche Diagnostic System, Inc., Branchburg, N.J.). HBV-DNA was detected according to a published method (Yeh et al. (2000) Hepatology 31, 1318).

3. Amplification of Serum DNA

Three primers were synthesized: P1, CCGCGG(N)$_4$ (SEQ ID NO:7); P2, GAATTC(N)$_4$ (SEQ ID NO:8); and P3, GCTTGCTCTGTCTC(T)$_{20}$ (SEQ ID NO:9). Each of the 4 N's in P1 and P2 was a mixture of A, T, C, and G in equal ratios. Serum DNA of patient-L was extracted using a previously published method (Yeh et al. (2000) Hepatology 31, 1318). PCR was performed using random hexamers for 25 cycles and then any two of P1–3 primers. The resulting products were cloned into a vector, pCR2.1-TOPO (Invitrogen, Carlsbad, Calif.).

4. Elimination of Clones Containing Human Genomic Sequences

To eliminate clones containing human genomic sequences, all clones were lifted onto a nitrocellulose filter and hybridized with a mixture of probes generated from total liver RNA.

Briefly, single-stranded probes were generated from cytoplasmic RNA extracted from a normal human liver tissue. The tissue was minced into small pieces, and lysed in a buffer containing 10 mM Tris hydrochloride (pH 7.2), 150 mM NaCl, and 0.5% Nonidet® P-40. The lysate was centrifuged at 1500×g for 5 min and the supernatant was collected. Total RNA was extracted from the supernatant. Reverse transcription (RT) was performed using SuperScript® II RNase H minus Reverse Transcriptase (Invitrogen Corporation, Calsbad, Calif.) and oligo(dT) as the RT primer. One-third of dTTP in the dNTP mixture was replaced with digoxigenin-11-dUTP (Boehringer Mannheim, Germany) to generate digoxigenin-labeled probes. The probes were mixed (1:2 in molar ratio) with oligo(dA) at 40° C. for 1 hr before hybridization.

The hybridization signal was detected using a DIG Luminescent Detection Kit (Boehringer Mannheim, Germany). For each batch of hybridization, 1 ng of pDR2 without any cDNA insert was used as a negative control and 1 pg of pDR2 containing a fragment of human albumin gene (Hs.184411) was used as a positive control. The negatively hybridized clones were considered to contain sequences of non-human origin.

5. Automatic Sequencing

Clones containing sequences of non-human origin were subject to automatic DNA sequencing (CEQ 2000; Beckman Instruments, Inc., Fullerton, Calif.). The sequence data were further searched against the NCBI human genome data bank on the World Wide Web at ncbi.nlm.nih.gov/genome/seq/HsBlast.html to eliminate clones containing human sequences.

Results

1. Detection of a DNA Fragment of Non-human Origin in Patient-L

A DNA fragment (NV-F) containing an open reading frame with incomplete 5' and 3' ends was identified. This sequence is not present in the NCBI human genome data bank.

Four primers, NV-F1 to 4, were used for nested PCR. NV-F1 (SEQ ID NO:3; nucleotides 4–23 of SEQ ID NO:1) and NV-F4 (SEQ ID NO:4; complementary to nucleotides 288–269 of SEQ ID NO:1) were used for the first round PCR; NV-F2 (SEQ ID NO:5; nucleotides 26–45 of SEQ ID NO:1) and NV-F3 (SEQ ID NO:6; complementary to nucleotides 267–248 of SEQ ID NO:1) were used for the second round PCR. The results showed that the NV-F sequence is not present in DNA extracted from HepG2 cells or human peripheral blood mononuclear cells from three different sources.

2. Detection of NV-F Sequence in Patients by PCR

Serum samples from 5 groups of subjects were analyzed for the presence of the NV-F sequence. The sequence was detected in 6.7% of healthy individuals, 23.5% of patients with chronic non-A–E hepatitis, 54% of patients with chronic hepatitis B, 44% of patients with chronic hepatitis C, and 23.3% of patients with colon cancer, respectively.

3. NV-F is a DNA Molecule

Nucleic acid was extracted from the serum sample of patient-L using either a DNA or RNA extraction method. The nucleic acid was digested, respectively, with DNase I or RNase A before analysis by PCR. The results showed that NV-F sequence is only present in the nucleic acid extracted using a DNA extraction method. Further, the NV-F molecule is resistant to RNase A digestion but sensitive to DNase I digestion.

4. CsCl Gradient Analysis

A serum sample containing both NV-F sequence and hepatitis B virus (from hepatitis B group of patients) was used for CsCl gradient analysis. The serum were loaded on a 20–50% CsCl density gradient and centrifuged in a Beckman SW41 rotor at 38K rpm for 20 h. The gradients were then fractionated and analyzed for HBsAg activities and for the presence of the NV-F sequence (by one round of PCR). The PCR product was analyzed by electrophoresis and Southern blot. The NV-F sequence was found in two fractions: the 1.33–1.39 g/ml fraction, and the 1.21–1.25 g/ml fractions, suggesting that the NV-F sequence belongs to a virus-like agent.

OTHER EMBODIMENTS

All of the features disclosed in this specification may be combined in any combination. Each feature disclosed in this specification maybe replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

---

What is claimed is:

1. An isolated nucleic acid comprising a nucleotide sequence at least identical to SEQ ID NO:1, or a complementary sequence thereof, wherein presence of the nucleic acid in a subject predisposes the subject to non-A–E hepatitis, hepatitis B, hepatitis C, or colon cancer, or a combination thereof.

2. An isolated nucleic acid characterized in that it hybridizes under stringent conditions to SEQ ID NO:1, or a complementary sequence thereof wherein the nucleic acid encodes a polypeptide having the sequence of SEQ ID NO: 2 and presence of the nucleic acid in a subject predisposes the subject to non-A–E hepatitis, hepatitis B, hepatitis C, or colon cancer or a combination thereof.

3. Cultured cell comprising the nucleic acid of claim 1, wherein the cell expresses the nucleic acid.

4. A cultured cell comprising the nucleic acid of claim 2, wherein the cell expresses the nucleic acid.

* * * * *

SEQUENCE LISTING

```
<160> NUMBER OF SEQ ID NOS: 9

<210> SEQ ID NO 1
<211> LENGTH: 364
<212> TYPE: DNA
<213> ORGANISM: Unknown
<220> FEATURE:
<221> NAME/KEY: CDS
<222> LOCATION: (1)...(364)
<223> OTHER INFORMATION: Viral sequence NV-F

<400> SEQUENCE: 1 gac tgt tgg tgg cac aaa gcc ccg agc aaa gtt ggc aac ccc cgc cgt      48
Asp Cys Trp Trp His Lys Ala Pro Ser Lys Val Gly Asn Pro Arg Arg
  1               5                  10                  15 cac tca gcc ctg caa gaa gcc act tgc gtc ctc cac aac tcc cca aag      96
His Ser Ala Leu Gln Glu Ala Thr Cys Val Leu His Asn Ser Pro Lys
             20                  25                  30 ttg tta ctg gtg tac caa tcg gag gca gcc gag ggg atg tat aaa gaa     144
Leu Leu Leu Val Tyr Gln Ser Glu Ala Ala Glu Gly Met Tyr Lys Glu
         35                  40                  45 ata gca aag gaa ttc gcg aaa ggg aaa gga aag aag gag agg aaa cta     192
Ile Ala Lys Glu Phe Ala Lys Gly Lys Gly Lys Lys Glu Arg Lys Leu
     50                  55                  60 aag aag aaa aaa atg ctt tcg ggt att acg gaa gaa ggt tct cca cag     240
Lys Lys Lys Lys Met Leu Ser Gly Ile Thr Glu Glu Gly Ser Pro Gln
 65                  70                  75                  80 cag tcc tct tct gct ccg ggc ctg gag gga gag agc gag acc aca aag     288
Gln Ser Ser Ser Ala Pro Gly Leu Glu Gly Glu Ser Glu Thr Thr Lys
                 85                  90                  95 atg atg agc aaa aaa ttc caa gac atg acg aat ccg caa aag aag aaa     336
Met Met Ser Lys Lys Phe Gln Asp Met Thr Asn Pro Gln Lys Lys Lys
            100                 105                 110 aag aaa cgg acc agt ctg ctc ctt aac t                               364
Lys Lys Arg Thr Ser Leu Leu Leu Asn
        115                 120

<210> SEQ ID NO 2
<211> LENGTH: 121
<212> TYPE: PRT
<213> ORGANISM: Unknown
<220> FEATURE:
<223> OTHER INFORMATION: Viral sequence NV-F

<400> SEQUENCE: 2
```

Asp Cys Trp Trp His Lys Ala Pro Ser Lys Val Gly Asn Pro Arg Arg
1               5                   10                  15

His Ser Ala Leu Gln Glu Ala Thr Cys Val Leu His Asn Ser Pro Lys
            20                  25                  30

Leu Leu Leu Val Tyr Gln Ser Glu Ala Ala Glu Gly Met Tyr Lys Glu
        35                  40                  45

Ile Ala Lys Glu Phe Ala Lys Gly Lys Gly Lys Glu Arg Lys Leu
    50                  55                  60

Lys Lys Lys Lys Met Leu Ser Gly Ile Thr Glu Glu Gly Ser Pro Gln
65              70                  75                  80

Gln Ser Ser Ser Ala Pro Gly Leu Glu Gly Glu Ser Glu Thr Thr Lys
                85                  90                  95

Met Met Ser Lys Lys Phe Gln Asp Met Thr Asn Pro Gln Lys Lys
            100                 105                 110

Lys Lys Arg Thr Ser Leu Leu Leu Asn
        115                 120

```
<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
tgttggtggc acaaagcccc                                              20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
ctttgtggtc tcgctctctc                                              20

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
gcaaagttgg caaccccgc                                               20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
ctccaggccc ggagcagaag                                              20

<210> SEQ ID NO 7
<211> LENGTH: 10
<212> TYPE: DNA
<213> ORGANISM: Artificial Sequence
<220> FEATURE:
```

-continued

```
<223> OTHER INFORMATION: Primer
<220> FEATURE:
<221> NAME/KEY: misc_feature
<222> LOCATION: 7-10
<223> OTHER INFORMATION: n = mixture of A, T, C, and G in equal ratios

<400> SEQUENCE: 7 ccgcggnnnn                                                                10

<210> SEQ ID NO 8
<211> LENGTH: 10
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 7-10
<223> OTHER INFORMATION: n = mixture of A, T, C, and G in equal ratios.

<400> SEQUENCE: 8 gaattcnnnn                                                                10

<210> SEQ ID NO 9
<211> LENGTH: 34
<212> TYPE: DNA
<213> ORGANISM: Artificial Sequence
<220> FEATURE:
<223> OTHER INFORMATION: Primer

<400> SEQUENCE: 9
gcttgctctg tctctttttt tttttttttt tttt                                     34
```